United States Patent [19]

Beyer, Jr.

[11] Patent Number: 4,663,322

[45] Date of Patent: May 5, 1987

[54] ANTIHYPERTENSIVE HYPERURETIC AND SALURETIC AGENT COMBINATIONS

[76] Inventor: Karl H. Beyer, Jr., P.O. Box 387, Penllyn, Pa. 19422

[21] Appl. No.: 792,236

[22] Filed: Oct. 29, 1985

Related U.S. Application Data

[63] Continuation of Ser. No. 336,736, Jan. 4, 1982, abandoned.

[51] Int. Cl.$^4$ .................... A61K 31/54; A61K 31/495
[52] U.S. Cl. ..................................... 514/222; 514/255
[58] Field of Search .............................. 514/255, 222

[56] References Cited

U.S. PATENT DOCUMENTS 3,313,813  4/1967  Cragoe ............................... 544/407
3,345,372  10/1967  Hanifin et al. ................... 544/407 X

OTHER PUBLICATIONS

*Physicians' Desk Reference*, 40th Ed., 1986, pp. 1199–1200.
Beyer, K., et al., *Pharmacol. Rev.*, 34: 287–313, 1983.
Saito, I, et al., *Cardiovasc. Res.*, 10: 149–152, 1976.
Beyer, K., *Clin. Therap.*, 1: 425–443, 1978.
Zanchetti, A., et al., *Am. J. Cardiol.*, 37: 675–691, 1976.
Singh, B., et al., *Brit. Med. J.*, 1: 143–146, 1967.
Gombos, E., et al., *New Eng. J. Med.*, 275: 1215–1220, 1966.
Kampffmeyer, H., et al., *Clin. Pharmacol. Therap.*, 9: 350–354, 1968.
McCaa, R., et al., *Adv. Exp. Med. Biol.*, 130: 227–255, 1980.
Weber, M., et al., *Arch. Int. Med.*, 137: 284–289, 1977.
Vaughan, E., et al., *Circ. Res.*, 42: 376–381, 1978.
Esler, M., et al., *Am. J. Cardiol.*, 36: 708–715, 1975.
Morganti, A., et al., *Am. J. Cardiol.*, 43: 600–604, 1979.

Sweet, C., et al., *Clin. Sci. Mol. Med.*, 48: 147–151, 1975.
Amery, A., et al., *New Eng. J. Med.*, 295: 1198–1199, 1976.
Morrison, R., et al., *Organic Chemistry*, 3rd Ed., Allyn and Bacon, Boston, 1973, p. 817.
*Chemical Abstracts*, 82:80803v (1975) [Mendelzon, J., et al., *Rev. Argent. Cardiol.*, 1974, 42(4), 278, 280, 282, 284, 289–90].
*Chemical Abstracts*, 88:45134e (1978) [Schena, F., et al., *Clin. Ter.*, 1977, 82(5), 489–94].
*Chemical Abstracts*, 85:177484s (1976) [Kubo, K., et al., Japan, Kokai 76 52,185, 5/8/76].
Benos, D., et al., *J. Gen. Physiol.*, 68(1): 43–63 (1976).

*Primary Examiner*—Richard A. Schwartz
*Attorney, Agent, or Firm*—Oblon, Fisher, Spivak, McClelland & Maier

[57] ABSTRACT

Hyperuretic agents of the formula:

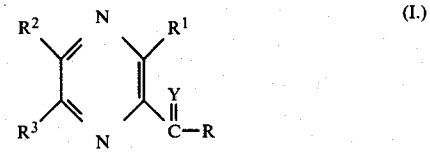

wherein
Y is O or NH;
R is OH; NHCONR$^4$R$^5$; or N=C(NR$^4$R$^5$)$_2$;
R$^1$ and R$^2$ are hydrogen, amino, or mono- or disubstituted amino, provided that R$^1$ and R$^2$ may not both be amino or substituted amino; and
R$^3$ is hydrogen or halo;

in combination with saluretic agents such as hydrochlorothiazide; are useful for treating hypertension.

16 Claims, No Drawings

ANTIHYPERTENSIVE HYPERURETIC AND SALURETIC AGENT COMBINATIONS

This application is a continuation of application Ser. No. 336,736 filed Jan. 4, 1982, now abandoned.

BACKGROUND OF THE INVENTION

1. Field of the Invention

The present invention is concerned with the combination of certain pyrazinoic acid derivatives useful as hyperuretic agents and various saluretic agents; and with pharmaceutical compositions and methods of treating hypertension in which the active ingredient employed is a combination of one of said pyrazinoic acid derivatives and a saluretic agent.

In mammals, including man, urea is the principal end product of nitrogen metabolism. Urea is synthesized in the body through the intermediation of the ornithine-urea cycle as from the more toxic ammonia and carbon dioxide. Some twenty-five grams of urea are synthesized in the human body per day and excreted primarily by way of the kidneys.

Urea and sodium (chloride) constitute the principal osmotically active constituents of the body. Whereas this osmotic role is similar for the two, urea and salt, they differ in important respects. Sodium chloride must be obtained from some exogenous source, and the distribution of sodium is essentially limited to extracellular fluid, including plasma water. Urea is synthetized by the body in large amounts, and its distribution is both intracellular and extracellular—being equivalent to total body water. (Potassium serves the intracellular osmotic role assumed by sodium extracellularly.)

When excess sodium is consumed, or retained by less than adequate renal function, iso-osmotic pressure is sustained by thirst-stimulated increased fluid consumption and by fluid retention which may lead to increased blood pressure and/or edema.

In the presence of impaired renal function sufficient to reduce urea excretion, its accumulation may be enough to cause increased intracellular as well as extracellular fluid accumulation, if iso-osmotic relationships are sustained by fluid accumulation. In severe circumstance, uremia may result. It is this intracellular/extracellular accumulation of fluid that is most likely to account for the symptomatology as well as the signs of uremia. At sub-uremic elevations of urea and body water levels the symptomatology may well be confused with salt retention, in which case therapy based on saluresis or hyperuresis may be used interchangeably—to some extent.

The present state of clinical knowledge recognizes that urea is filtered with plasma water at the glomeruli of the kidney and that a portion of that filtered urea undergoes passive back diffusion in the course of urine formation by the nephron. The passive back diffusion of urea can be reduced by increasing the transit rate, i.e., increasing the urine flow.

Increased transit rate can be induced (1) by expanding body fluid volume, which is self-defeating from a therapeutic standpoint; (2) with the aid of an osmotic diuretic, e.g., mannitol, which is impractical because of the need to administer large amounts parenterally, or (3) temporarily, by the use of potent saluretic agents at dosages sufficient to alter electrolyte balance.

In accordance with the present invention, it has been discovered that the mammalian kidney is capable of actively secreting and reabsorbing urea in addition to being filtered at the glomeruli and undergoing passive back diffusion.

Moreover, it has been discovered that the pyrazinoic acid derivatives utilized in the present invention are capable of inhibiting the active renal tubular reabsorption of urea, predominantly; whereas other pyrazinoic acid derivatives such as the fluoro analog of amiloride inhibit preponderantly active tubular secretion of urea without significantly inhibiting active reabsorption of urea. In so doing they lower urea blood levels and increase the osmotic concentration of urine as indications of their capability of influencing osmotically modulated functions of cells and cell membranes. These may thus be called osmoregulatory agents to identify their role in therapy. Combined with various saluretic agents, their usefulness is considered to extend from the management of mild hypertension and pulmonary edema to the neurological symptomatology of malignant or severe hypertension.

2. Brief Description of the Prior Art

Cragoe U.S. Pat. No. 3,313,813 describes 3-amino-5,6-disubstituted-pyrazinoyl guanidines and their use as diuretic, natriuretic agents which selectively enhance the excretion of sodium ions without causing an increase in excretion of potassium ions.

Benos et al. in J. Gen. Physiol. 68(1): 43–63 (1976) describe the effect of amiloride and some of its analogs on cation transport in isolated frog skin and thin lipid membranes.

However, none of the above references in any way suggests the use of the particular pyrazinoic acid derivative hyperuretic agents utilized in the present invention for treating hypertension, eclampsia, uremia, and the like, since these references fail to suggest the hyperuretic activity of said pyrazinoic acid derivatives, and since said derivatives do not have sufficient saluretic and antikaluretic activity to be useful in accordance with the requirements described in said references.

DETAILED DESCRIPTION OF THE INVENTION AND PREFERRED EMBODIMENTS

In accordance with the present invention there is provided a pharmaceutical composition for treating hypertension and edema comprising a pharmaceutically acceptable carrier and a therapeutically effective amount of the combination of (a) a compound of the formula:

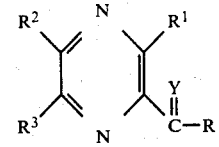

(I.)

wherein
Y is O or NH,
R is OH; $NHCONR^4R^5$; or $N=C(NR^4R^5)_2$; where $R^4$ and $R^5$ are each independently selected from the group consisting of hydrogen; $C_{1-10}$ alkyl, straight or branched chain; aryl $C_{1-4}$ alkyl; mono- or disubstituted aryl $C_{1-4}$ alkyl where the substituents are fluoro, chloro, bromo, iodo, or $C_{1-10}$ alkyl, straight or branched chain;
$R^1$ and $R^2$ are each independently selected from the group consisting of hydrogen, amino, and mono- or disubstituted amino where the substituents are $C_{1-10}$ alkyl, straight or branched chain, or $C_{3-8}$ cycloalkyl; provided that $R^1$ and $R^2$ may not both be amino or substituted amino; and $R^3$ is hydrogen; fluoro; chloro; bromo; or iodo; and a pharmaceutically acceptable salt thereof; and (b) a saluretic agent selected from the group consisting essentially of ethacrynic acid; furosemide; bumetanide; muzolimine; benzothiadiazines including chlorothiazide and hydrochlorothiazide; chlorothalidone; quinethazone; metholazone; indacrinone; acetazolamide; ethoxyzolamide; and methazolamide.

Preferred combinations of the present invention are those wherein for the compound of Formula I Y is O or NH; one of $R^1$ and $R^2$ is hydrogen or amino and the other is hydrogen; and $R^3$ is hydrogen; and the saluretic agent is hydrochlorothiazide.

Particularly preferred compounds of Formula I are the following:

pyrazinoylguanidine;

3-aminopyrazinoylguanidine.

The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanote, hydrochloride, hydrobromide, hydroiodide, 2-hydroxyethanesulfonate, lactate, maleate, methansulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The pyrazinoic acid derivatives and saluretic agent combinations of the present invention possess a high degree of hyperuretic and saluretic/diuretic activity. They are of value in the treatment of hypertension and edema.

For these purposes the combinations of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the combinations of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3 butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The combinations of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the active ingredient are employed.

For the compounds of Formula I, dosage levels of the order of 25 to 750 mg. per day are useful in the treatment of the above indicated conditions. For example, hypertension is effectively treated by the administration of from about 0.5 to 15 15 mg. of a compound of Formula I per kilogram of body weight per day. Advantageously from about 1 to about 15 mg. per kilogram of body weight and especially from about 2 to about 10 mg. per kilogram daily dosage produces highly effective results.

Dosage levels for the saluretic agent component of the combinations of the present invention will generally be in accordance with established dosages for these agents as independent therapeutics.

The amount of active ingredient that may be combined with the carrier materials to produce a single dosage form will vary depending upon the host treated and the particular mode of administration. For example, a formulation intended for the oral administration of humans may contain from 25 to 750 mg. of active agent compounded with an appropriate and convenient amount of carrier material which may vary from about 5 to about 95 percent of the total composition. Dosage unit forms will generally contain between from about 25 to about 500 mg. of active ingredient.

It will be understood, however, that the specific dose level for any particular patient will depend upon a variety of factors including the activity of the specific compound employed, the age, body weight general health, sex, diet, time of administration, route of administration, rate of excretion, drug combination and the severity of the particular disease undergoing therapy.

In accordance with the present invention there is further provided a method of treating hypertension comprising administering to a host in need of such treatment a therapeutically effective amount of the combination of (a) a compound of the formula:

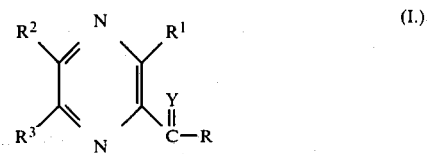

wherein Y, R, $R^1$, $R^2$, and $R^3$ have the same meaning as above; and (b) a saluretic agent selected from the group consisting essentially of ethacrynic acid; furosemide; bumetanide; muzolimine; benzothiadiazines including chlorothiazide and hydrochlorothiazide; chlorothalidone; quinethazone; metholazone; indacrinone; acetazolamide; ethoxyzolamide; and methazolamide.

In accordance with the present invention there is still further provided a method of treating edema comprising administering to a host in need of such treatment a therapeutically effective amount of the combination of (a) a compound of the formula:

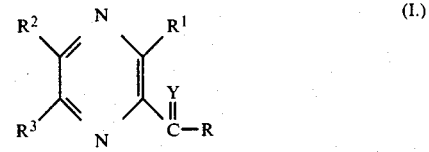

wherein Y, R, $R^1$, $R^2$, and $R^3$ have the same meaning as above; and (b) a saluretic agent selected from the group consisting essentially of ethacrynic acid; furosemide; bumetanide; muzolimine; benzothiadiazines including chlorothiazide and hydrochlorothiazide; chlorothalidone; quinethazone; metholazone; indacrinone; acetazolamide; ethoxyzolamide; and methazolamide.

The compounds of Formula I in the combination of the present invention inhibit urea net reabsorption in a dose-related manner that includes increased excretion of sodium, chloride and potassium. Their effect is independent of urine flow, and under conditions where passive back diffusion is minimized they increase urea clearance to approximate glomerular filtration rate.

There is resident in pyrazinoic acid derivatives a variable capability to inhibit secretion of urea into the lumen of the renal tubule. This is minimal in the pyrazinoylguanidines of the present invention, which does not manifest that effect in Dalmatians; whereas the fluoro analog of amiloride almost completely inhibits urea secretion and fluid excretion even when back diffusion is minimized. In stop-flow experiments, inhibition of active reabsorption and secretion can be demonstrated.

The compounds of Formula I utilized in the present invention are active on oral as well as parenteral administration. 3-Aminopyrazinoylguanidine is most effective promptly, whereas pyrazinoylguanidine effect and blood level requires perhaps an added hour for maximal effect.

As already indicated, the compounds of Formula I utilized in the present invention may properly be called osmoregulatory agents. Osmoregulation, in turn, involves several interrelated factors.

Salts, as the sum of sodium, chloride and bicarbonate ions, supplies some 93% of the 300 milli Osmols/L of extra-cellular water in humans. Urea supplies about 1.3% of that osmotic force, normally. Of the other constituents, only glucose at 1.8% is a factor in osmoregulation.

Thus, osmoregulation of water volume to sustain isotonicity is by thirst and by the action of the antidiuretic hormone on the most distal portion of the nephron to modulate water reabsorption. Whereas there is an appetite for salt regulation, the kidney seems designed to maximize sodium conservation. The search for a salt regulating hormone continues, but the only known "active" sodium reabsorptive mechanisms in the kidney involve the availability of hydrogen ions and/or the aldosterone-availability modulated availability of potassium for exchange with sodium across the nephron. Sodium rarely becomes a means for increasing water excretion, unless its reabsorption is decreased by the action of natriuretic or saluretic diuretic agents.

One other homeostatic mechanism, the so-called sodium pump, or sodium-potassium-magnesium-dependent ATP-ase mechanism common to cell membranes, serves to relegate the osmoregulatory effect of sodium on fluid volume primarily to extracellular space, or about 25% of total cellular and extra-cellular volume. Thus, exquisitely small increases in sodium retention are capable of expanding extra-cellular volume, thus increasing blood pressure and glomerular filtration rate, without substantial involvement of cell volume.

On the other hand, the osmoregulation of thirst by the cells of the neurohypophysis is not so sensitive to urea concentration. As ADH influences water reabsorption, so does it alter urea back diffusion by the kidney. Conversely, in the course of the human kidney normally excreting some 25 grams of urea per day, that substance serves as the principal osmoregulator of water excretion.

The plasma concentration of urea can be influenced by both protein intake and by renal tubular reabsorption of a portion of the amount filtered by the glomeruli. Thus, a high protein diet normally increases both urea and water excretion. Low protein intake or reduced glomerular filtration rate decreases urea and fluid output. As an approximation, if glomerular filtration rate is reduced to half normal, plasma water concentration of urea will double on a given protein intake. The consequence is to expand intracellular volume as well as extracellular by a ratio of 45:25 or 1.8, assuming a constant osmotic pressure relationship exists between the two spaces. The reason for this important difference between the two spaces is that while sodium is essentially limited to extra-cellular space, urea is distributed more or less uniformly throughout body water. Thus, the patient whose urea plasma concentration is twice normal and whose extracellular volume is expanded carries a greater total expanded volume than if the urea level was normal. What may be considerably more important than the increased total volume is how that increased "intra-cellular" fluid is distributed within the cells, their membranes, the compartmentalization of their structure.

In view of the foregoing relationship between urea and salt, it should follow that saluretic diuretic therapy would be an adequate control of fluid retention in the absence of hyperuremia. When elevated urea plasma concentration co-exists with fluid retention, or hypertension that responds to saluretic agent administration, then it would seem rational to induce increased urea excretion—to reduce its blood level.

Increased urea blood level in cardiovascular renal disease is more common than appreciated. Whereas increased urine flow increases urea excretion, diuretics and adrenergic blocking agents are more likely to increase urea blood levels. In view of this proposed reciprocal relationship of salt and urea retention, saluretic diuretic treatment of hypertension represents only half of a rational therapeutic measure—combined saluretic-hyperuremic therapy. In accordance with the present invention, therefore, use of the pyrazinoic acid derivatives of Formula I and the saluretic agents described herein makes possible a greater direct control of electrolyte and water balance, i.e., homeostasis, and expands the utility of present therapy by providing direct regulation of tissue fluid as well as extracellular fluid. The present invention provides a new and expanded way of looking at the management of electrolyte and water balance in terms of osmoregulation.

Accordingly, the present invention provides for sustained therapy in the treatment of hypertension; postoperative treatment for the relief of tissue accumulation of fluids without risk of disturbed acid-base balance; and treatment of pulmonary edema.

The following example, which was actually carried out, will serve to illustrate the hyperuretic activity of the pyrazinoic acid derivatives with and without a saluretic agent, hydrochlorothiazide.

EXAMPLE

In Tables I and II are presented the effect of first pyrazinoylguanidine then both pyrazinoylguanidine and hydrochlorothiazide (Table I) and, alternatively, the effect of hydrochlorothiazide then hydrochlorothiazide and pyrazinoylguanidine on excretion of urea and the inorganic electrolytes (Table II) in the dog. Prior to the duplicate control 20 minute clearances, creatinine was injected subcutaneously and an isotonic mannitol-$PO_4$ buffer venoclysis was begun and continued throughout the experiment at 1 ml/min. Immediately after the second control clearance either pyrazinoylguanidine was added to the venoclysis at 3 mg/kg/h plus 2 mg/kg prime I.V. or hydrochlorothiazide was added at a rate of 1.5 mg/kg/h plus 1 mg/kg prime. In either instance, after 30 minutes a succession of three 20-minute clearances were conducted. Immediately thereafter, the mannitol infusion was changed to one containing both pyrazinoylguanidine and hydrochlorothiazide at the dosages specified for the first drug phase. Thirty minutes later, three more 20-minute clearances were performed. Blood and urine were subjected to the customary analyses.

If the first drug phase of Tables I and II are compared, the typical effects of the two compounds are evident. Pyrazinoylguanidine increased urea excretion and reduced its plasma concentration disproportionate to the increased urine flow. It increased sodium, potassium and chloride excretion, but the effect of hydrochlorothiazide on sodium, potassium, chloride and osmolar excretion was approximately twice that of pyrazinoylguanidine. Any marginal effect of hydrochlorothiazide on the urea parameters was due to the increase in urine flow attributable to the greater saluresis.

When the two compounds were combined in the second drug phase, the sum of their effects were evident in both Tables I and II. The effect on urea was increased somewhat by the greater diuresis plus the pyrazinoylguanidine, and the compounds combined to increase sodium, chloride, potassium and osmolar output and urine flow.

The data discussed above is set out in Tables I and II below:

TABLE I

Effect of pyrazinoylguanidine alone then coadministered with hydrochlorothiazide on the excretion of urea, Na, Cl, K by the dog.

| Urine Vol. ml/min | pH | GFR | UREA P mg % | UV/P ml/min | CR | Na UV μeq/min | Cl UV μeq/min | K UV μeq/min | Urine mOsm/min |
|---|---|---|---|---|---|---|---|---|---|
| Exp. 4141; Dog Wt. 32.3 kg Control phase - isotonic mannitol-PO$_4$ venoclysis at 1 ml/min | | | | | | | | | |
| 0.3 | 7.0 | 78.5 | 18.5 | 25.9 | 0.33 | 22 | 18 | 13 | .202 |
| 0.2 | 6.9 | 74.6 | 18.7 | 24.6 | 0.33 | 23 | 18 | 13 | .189 |
| Pyazinoylguanidine 2 mg/kg I.V. Prime plus 3 mg/kg/h added to mannitol venoclysis at 1 ml/min | | | | | | | | | |
| 0.5 | 7.1 | 77.0 | 18.1 | 34.6 | 0.45 | 47 | 27 | 20 | .416 |
| 0.4 | 7.2 | 71.8 | 17.4 | 38.7 | 0.54 | 51 | 30 | 23 | .411 |
| 0.5 | 7.2 | 74.4 | 16.9 | 46.2 | 0.62 | 56 | 36 | 26 | .491 |
| Hydrochlorothiazide I.V. Prime 1 mg/kg, 1.5 mg/kg/h added to venoclysis containing pyrazinoylguanidine as above | | | | | | | | | |
| 1.2 | 7.3 | 70.6 | 16.6 | 50.8 | 0.72 | 140 | 109 | 58 | .942 |
| 1.3 | 7.3 | 73.0 | 16.5 | 54.7 | 0.75 | 168 | 135 | 68 | 1.174 |
| 1.4 | 7.3 | 75.5 | 16.5 | 57.3 | 0.76 | 189 | 155 | 67 | 1.267 |

TABLE II

Effect of hydrochlorothiazide alone then coadministered with pyrazinoylguanidine on the excretion of urea, Na, Cl, K by the dog.

| Urine Vol. ml/min | pH | GFR | UREA P mg % | UV/P ml/min | CR | Na UV μeq/min | Cl UV μeq/min | K UV μeq/min | Urine mOsm/min |
|---|---|---|---|---|---|---|---|---|---|
| Exp. 4071; Dog Wt. 19.1 kg Control phase - isotonic mannitol-PO$_4$ venoclysis at 1 ml/min | | | | | | | | | |
| 0.2 | 7.0 | 65.4 | 18.2 | 20.3 | 0.31 | 10 | 9 | 8 | .145 |
| 0.2 | 7.0 | 64.2 | 18.5 | 21.2 | 0.33 | 12 | 10 | 8 | .170 |
| Hydrochlorothiazide I.V. Prime 1 mg/kg, 1.5 mg/kg/h added to mannitol venoclysis at 1 ml/min | | | | | | | | | |
| 0.7 | 7.1 | 60.6 | 18.0 | 23.0 | 0.38 | 58 | 53 | 23 | .616 |
| 0.9 | 7.1 | 66.7 | 18.1 | 27.3 | 0.41 | 89 | 78 | 35 | .761 |
| 1.0 | 7.2 | 63.0 | 18.0 | 25.2 | 0.40 | 107 | 101 | 43 | .874 |
| Pyazinoylguanidine I.V. Prime 2 mg/kg, 3 mg/kg/h added to venoclysis containing hydrochlorothiazide as above | | | | | | | | | |
| 1.0 | 7.3 | 59.8 | 17.8 | 28.7 | 0.48 | 119 | 110 | 49 | .983 |
| 1.0 | 7.3 | 63.9 | 17.0 | 38.9 | 0.61 | 124 | 114 | 41 | .999 |
| 0.9 | 7.3 | 61.6 | 16.4 | 43.1 | 0.70 | 121 | 110 | 36 | .886 |

The pyrazinoic acid derivatives utilized in the present invention may be prepared in accordance with well known procedures, for example those described in U.S. Pat. No. 3,313,813.

What is claimed is:

1. An antihypertensive pharmaceutical composition in unit dosage form comprising a pharmaceutically acceptable carrier and the combination of:

(a) pyrazinoylguanidine, a pharmaceutically acceptable salt of pyrazinoylguanidine, 3-aminopyrazinoylguanidine, or a pharmaceutically acceptable salt of 3-aminopyrazinoylguanidine; and
   (b) a saluretic agent selected from the group consisting essentially of ethacrynic acid; furosemide; bumetanide; muzolimine; saluretic benzothiadiazines; chlorothalidone; quinethazone; metholazone; indacrinone; acetazolamide; ethoxyzolamide; and methazolamide.

2. The pharmaceutical composition of claim 1, comprising pyrazinoylguanidine.

3. The pharmaceutical composition of claim 1, comprising a pharmaceutically acceptable salt of pyrazinoylguanidine.

4. The pharmaceutical composition of claim 1, comprising 3-aminopyrazinoylguadine.

5. The pharmaceutical composition of claim 1, comprising a pharmaceutically acceptable salt of 3-aminopyrazinoylguanidine.

6. An antihypertensive composition, comprising the combination:

(a) pyrazinoylguanidine, a pharmaceutically acceptable salt of pyrazinoylguanidine, 3-aminopyrazinoylguanidine, or a pharmaceutically acceptable salt of 3-aminopyrazinoylguanidine; and (b) a saluretic agent selected from the group consisting essentially of ethacrynic acid; furosemide; bumetanide; muzolimine; soluretic benzothiadiazines; chlorothalidone; quinethazone; metholazone; indacrinone; acetazolamide; ehtoxyzolamide; and methazolamide.

7. The composition of claim 6, comprising pyrazinoylguanidine.

8. The composition of claim 6, comprising a pharmaceutically acceptable salt of pyrazinoylguanidine.

9. The composition of claim 6, comprising 3-aminopyrazinoylguanidine.

10. The composition of claim 6, comprising a pharmaceutically acceptable salt of 3-aminopyrazinoylguanidine.

11. The pharmaceutical composition of claim 1, comprising chlorothiazide or hydrochlorothiazide.

12. The pharmaceutical composition of claim 1, comprising chlorothiazide.

13. The pharmaceutical composition of claim 1, comprising hydrochlorothiazide.

14. The composition of claim 6, comprising chlorothiazide or hydrochlorothiazide.

15. The composition of claim 6, comprising chlorothiazide.

16. The composition of claim 6, comprising hydrochlorothiazide.

* * * * *